(12) United States Patent
Gelfand et al.

(10) Patent No.: US 10,925,530 B2
(45) Date of Patent: Feb. 23, 2021

(54) BLOOD SAMPLING TRANSFER DEVICE

(71) Applicant: Becton, Dickinson and Company, Franklin Lakes, NJ (US)

(72) Inventors: Craig A. Gelfand, Jackson, NJ (US); Gary D. Fletcher, Sparta, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 13 days.

(21) Appl. No.: 14/251,673

(22) Filed: Apr. 14, 2014

(65) Prior Publication Data
US 2014/0305823 A1 Oct. 16, 2014

Related U.S. Application Data

(60) Provisional application No. 61/811,918, filed on Apr. 15, 2013.

(51) Int. Cl.
*A61B 5/15* (2006.01)
*B01L 3/00* (2006.01)
(Continued)

(52) U.S. Cl.
CPC ...... *A61B 5/150213* (2013.01); *A61B 5/1411* (2013.01); *A61B 5/151* (2013.01); *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *A61M 1/36* (2013.01);
(Continued)

(58) Field of Classification Search
None
See application file for complete search history.

(56) References Cited

U.S. PATENT DOCUMENTS 3,322,114 A 5/1967 Portnoy et al.
3,640,393 A 2/1972 Hurtig
(Continued)

FOREIGN PATENT DOCUMENTS

CN 1382966 A 12/2002
CN 101102847 A 1/2008
(Continued)

OTHER PUBLICATIONS

Membrane Separation Technology for Research and Quality Control, Sartorius AG, Separation Technology, Laboratory Filtration; Mar. 1, 1997.

*Primary Examiner* — Matthew Kremer
(74) *Attorney, Agent, or Firm* — The Webb Law Firm

(57) ABSTRACT

A blood sampling transfer device that includes a lancing tape having a flow channel and a transfer cartridge removably connected to the lancing tape is disclosed. The blood sampling transfer device provides a closed system that reduces the exposure of a blood sample to both skin and environment and provides fast mixing of a blood sample with a sample stabilizer.

15 Claims, 16 Drawing Sheets

(51) Int. Cl.

| | | |
|---|---|---|
| *A61M 1/36* | (2006.01) | |
| *A61B 5/151* | (2006.01) | |
| *A61B 5/157* | (2006.01) | |
| *A61M 1/34* | (2006.01) | |
| *B04B 7/08* | (2006.01) | |
| *G01N 1/28* | (2006.01) | |
| *G01N 1/34* | (2006.01) | |
| *G01N 1/40* | (2006.01) | |
| *G01N 33/49* | (2006.01) | |

(52) U.S. Cl.
CPC ............ *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A * | 4/1985 | Nielsen | B01L 3/5021 422/533 |
| 4,627,445 A | 12/1986 | Garcia et al. | |
| 5,055,203 A | 10/1991 | Columbus | |
| 5,163,442 A * | 11/1992 | Ono | A61B 5/1411 600/565 |
| 5,219,999 A | 6/1993 | Suzuki et al. | |
| 5,422,018 A * | 6/1995 | Saunders | B01D 21/20 210/512.1 |
| 5,636,640 A | 6/1997 | Staehlin | |
| 5,726,026 A | 3/1998 | Wilding et al. | |
| 5,839,715 A | 11/1998 | Leinsing | |
| 5,922,591 A | 7/1999 | Anderson et al. | |
| 6,074,183 A | 6/2000 | Allen et al. | |
| 6,264,619 B1 * | 7/2001 | Ferguson | A61B 5/1405 206/569 |
| 6,506,167 B1 | 1/2003 | Ishimito et al. | |
| 6,869,405 B2 | 3/2005 | Marsden | |
| 8,158,410 B2 | 4/2012 | Tang et al. | |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0228259 A1 * | 10/2006 | Samsoondar | B01L 3/502715 422/82.05 |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

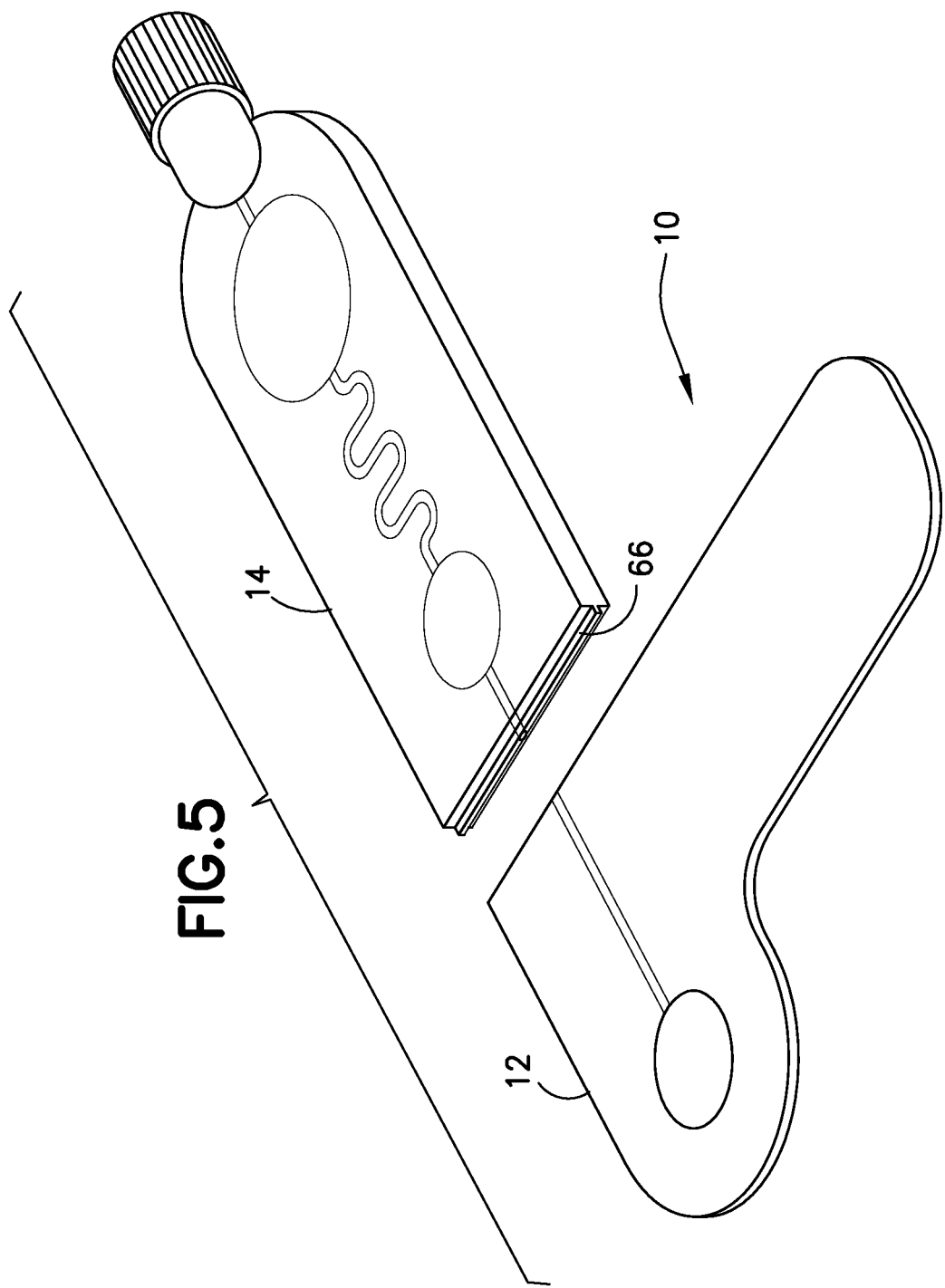

BLOOD SAMPLING TRANSFER DEVICE

CROSS-REFERENCE TO RELATED APPLICATION

The present application claims priority to U.S. Provisional Application No. 61/811,918, filed Apr. 15, 2013, entitled "Medical Device for Collection of a Biological Sample", the entire disclosure of which is hereby incorporated by reference.

BACKGROUND OF THE INVENTION

1. Field of the Disclosure

The present disclosure relates generally to devices, assemblies, and systems adapted for use with vascular access devices and capillary blood access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including, for example, chemical composition, hematology, and coagulation.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic strip or cartridge. Thereafter, the diagnostic cartridge, often using an associated instrument into which the strip or cartridge is inserted, analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from an already inserted vascularly located catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid sampling transfer device, such as a blood sampling transfer device, that includes a lancing tape having a flow channel and a transfer cartridge removably connected to the lancing tape. The blood sampling transfer device provides a closed system that reduces the exposure of a blood sample to both skin and environment and provides fast mixing of a blood sample with a sample stabilizer. The sample stabilizer, can be an anticoagulant, or a substance designed to preserve a specific element within the blood such as, for example, RNA, protein analyte, or other element.

In accordance with an embodiment of the present invention, a blood sampling transfer device includes a lancing tape having a flow channel and a transfer cartridge removably connected to the lancing tape, the transfer cartridge having a reservoir, wherein with the transfer cartridge connected to the lancing tape, the reservoir is in fluid communication with the flow channel, and wherein with the transfer cartridge disconnected from the lancing tape, the reservoir is sealed.

In one configuration, the lancing tape includes a target for a lancet device. In another configuration, the target of the lancing tape is aligned with the flow channel. In yet another configuration, the target of the lancing tape is a circular graphic indicator. In one configuration, the transfer cartridge includes a transfer cartridge flow channel in fluid communication with the reservoir. In another configuration, the transfer cartridge flow channel contains a sample stabilizer. In yet another configuration, the transfer cartridge includes a dispensing bulb in fluid communication with the transfer cartridge flow channel, the transfer cartridge flow channel being disposed between the dispensing bulb and the reservoir. In one configuration, the blood sampling transfer device includes a frangible portion between the transfer cartridge and the lancing tape, wherein the transfer cartridge is removably connected to the lancing tape via the frangible portion.

In accordance with another embodiment of the present invention, a blood sampling system includes a lancet device having a puncturing element; and a blood sampling transfer device including a lancing tape having a flow channel and a target aligned with the flow channel, the target for the puncturing element of the lancet device, and a transfer cartridge removably connected to the lancing tape, the transfer cartridge having a reservoir, wherein with the transfer cartridge connected to the lancing tape, the reservoir is in fluid communication with the flow channel, and wherein with the transfer cartridge disconnected from the lancing tape, the reservoir is sealed.

In one configuration, the target of the lancing tape is a circular graphic indicator. In another configuration, the transfer cartridge includes a transfer cartridge flow channel in fluid communication with the reservoir. In yet another configuration, the transfer cartridge flow channel contains a sample stabilizer. In one configuration, the transfer cartridge includes a dispensing bulb in fluid communication with the transfer cartridge flow channel, the transfer cartridge flow channel being disposed between the dispensing bulb and the reservoir. In another configuration, the blood sampling system includes a frangible portion between the transfer cartridge and the lancing tape, wherein the transfer cartridge is removably connected to the lancing tape via the frangible portion.

In accordance with another embodiment of the present invention, a biological fluid sampling system, such as a blood sampling system, includes a lancet device having a puncturing element; a blood sampling transfer device including a lancing tape having a flow channel and a target aligned with the flow channel, the target for the puncturing element of the lancet device, and a transfer cartridge removably connected to the lancing tape, the transfer cartridge having a reservoir, wherein with the transfer cartridge connected to the lancing tape, the reservoir is in fluid communication with the flow channel, and wherein with the transfer cartridge disconnected from the lancing tape, the reservoir is sealed; and a packaging member having a compartment sized and adapted to receive the lancet device and the blood sampling transfer device therein.

In one configuration, the packaging member includes a blister package. In another configuration, the lancing tape includes an adhesive on an inferior surface of the lancing tape.

In accordance with another embodiment of the present invention, a biological fluid separation system, such as a blood separation system, for a blood sample having a cellular portion and a plasma portion includes a blood sampling transfer device adapted to receive the blood sample, the blood sampling transfer device including a lancing tape having a flow channel and a transfer cartridge removably connected to the lancing tape, the transfer cartridge having a reservoir, wherein with the transfer cartridge connected to the lancing tape, the reservoir is in fluid communication with the flow channel, and wherein with the transfer cartridge disconnected from the lancing tape, the reservoir is sealed; and a centrifuge having a receiving port adapted to receive the transfer cartridge, wherein with the transfer cartridge received within the centrifuge and a rotational force applied to the transfer cartridge, the plasma portion of the blood sample is separated from the cellular portion through the reservoir.

In one configuration, the lancing tape includes an adhesive on an inferior surface of the lancing tape.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 4 is a cross-sectional view of a blood sampling transfer device taken along line 4-4 of FIG. 1 in accordance with an embodiment of the present invention.

FIG. 5 is a perspective view of a blood sampling transfer device with a transfer cartridge removed from a lancing tape in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
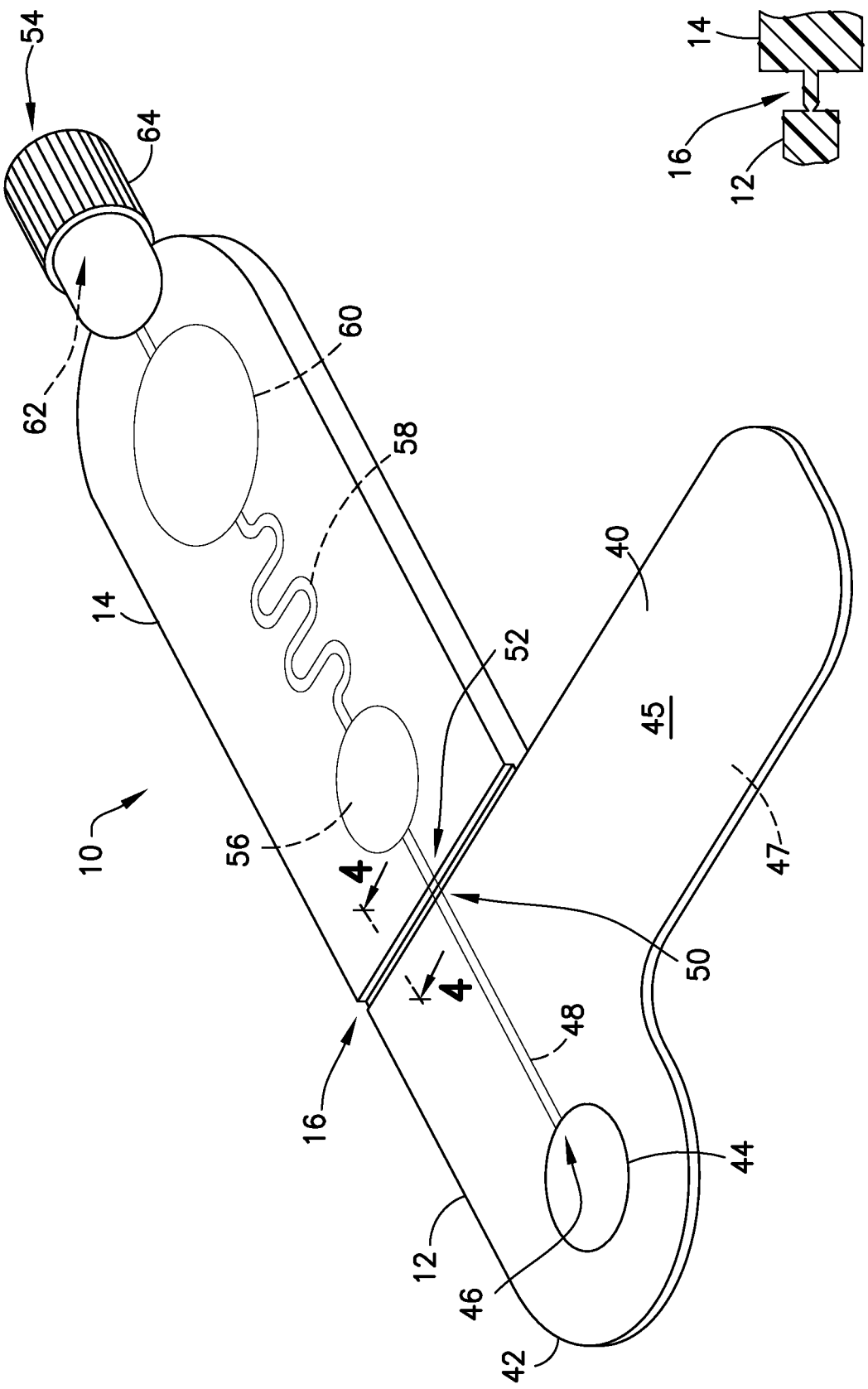
FIG. 1 is a perspective view of a blood sampling transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood at the point of care without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-6 illustrate an exemplary embodiment of the present disclosure. Referring to FIGS. 1-6, a biological fluid sampling transfer device, such as a blood sampling transfer device 10 of the present disclosure, includes a lancing tape 12 having a flow channel 48 and a transfer cartridge 14 removably connected to the lancing tape 12. The blood sampling transfer device 10 of the present disclosure provides a closed system that reduces the exposure of a blood sample and provides fast mixing of a blood sample with a sample stabilizer.

Figure 10:
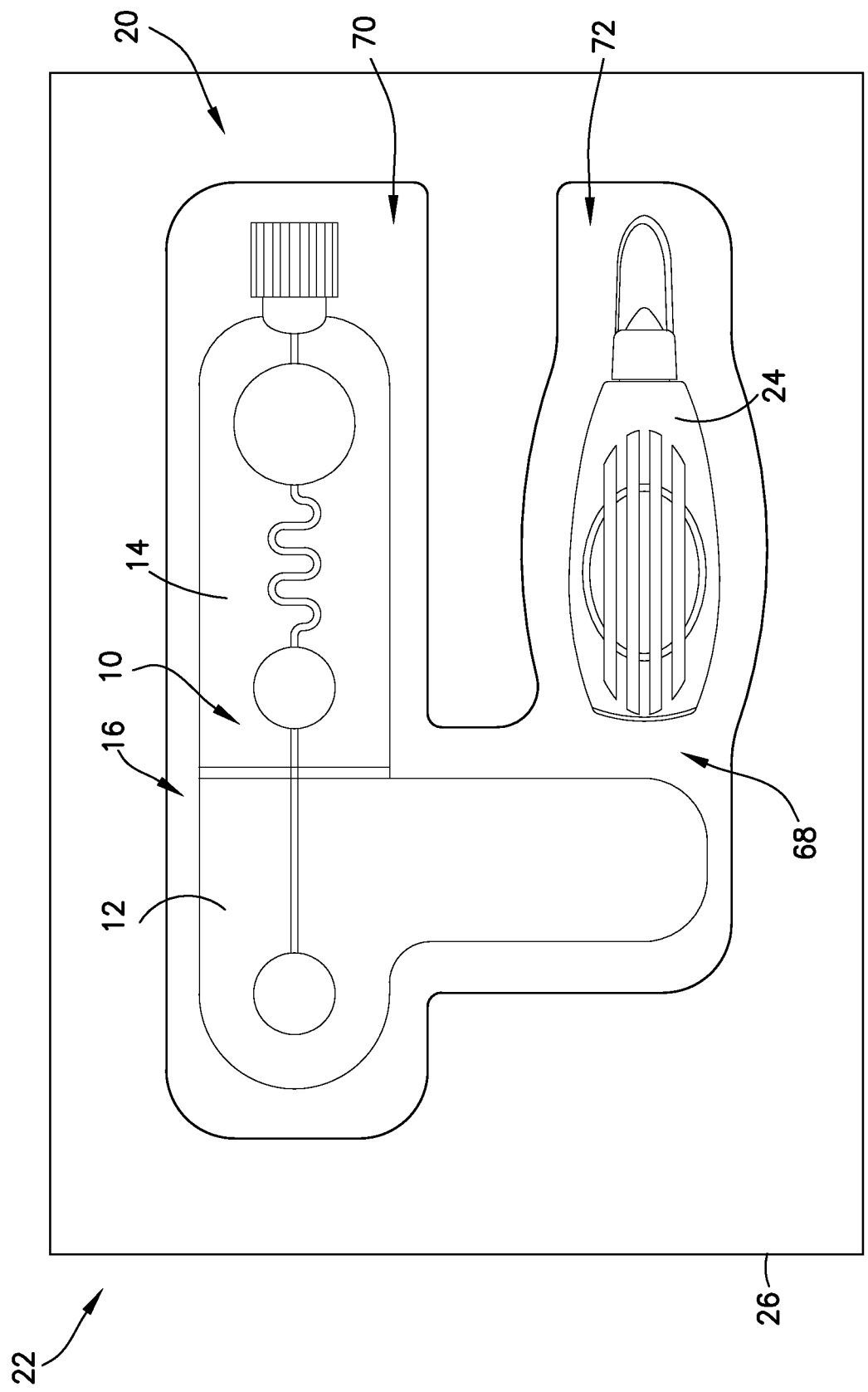
FIG. 10 is an elevation view of a blood sampling system in accordance with an embodiment of the present invention.

FIG. 10 illustrates an exemplary embodiment of the present disclosure. Referring to FIG. 10, a biological fluid sampling system, such as a blood sampling system 20 of the present disclosure, includes a kit 22 having a lancet device 24, a blood sampling transfer device 10 having a lancing tape 12 having a flow channel 48 and a transfer cartridge 14 removably connected to the lancing tape 12, and a packaging member 26 having a compartment 68 sized and adapted to receive the lancet device 24 and the blood sampling transfer device 10 therein.

Figure 15:
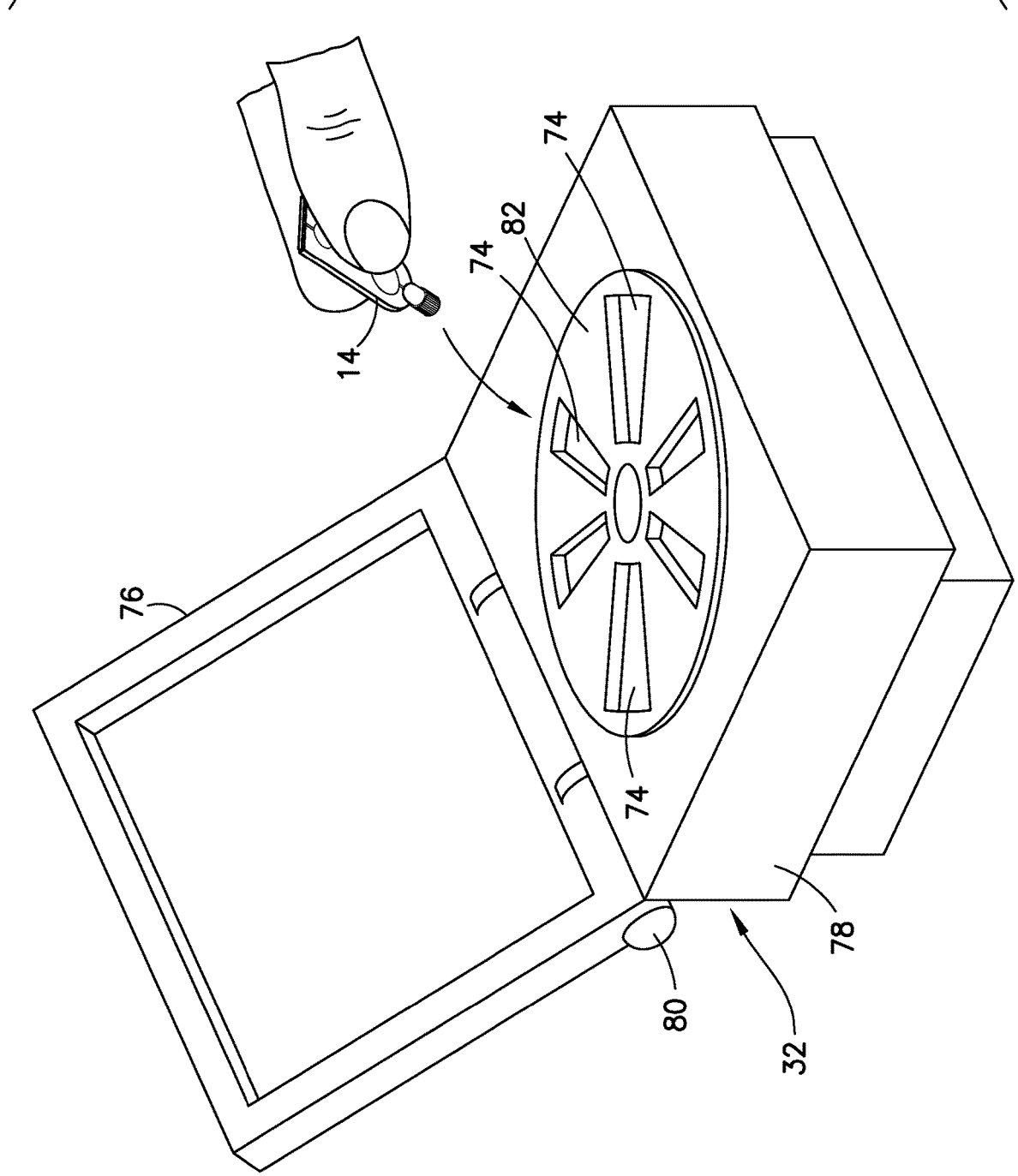
FIG. 15 is a perspective view of a blood separation system in accordance with an embodiment of the present invention.

FIG. 15 illustrates an exemplary embodiment of the present disclosure. Referring to FIG. 15, a blood separation system 30 of the present disclosure for a blood sample includes a blood sampling transfer device 10 adapted to receive a blood sample and having a lancing tape 12 having a flow channel 48 and a transfer cartridge 14 removably connected to the lancing tape 12, and a centrifuge 32 having a receiving port 74 adapted to receive the transfer cartridge 14 such that with the transfer cartridge 14 received within the centrifuge 32 and a rotational force applied to the transfer cartridge 14, a plasma portion of the blood sample is separated from a cellular portion.

Figure 11:
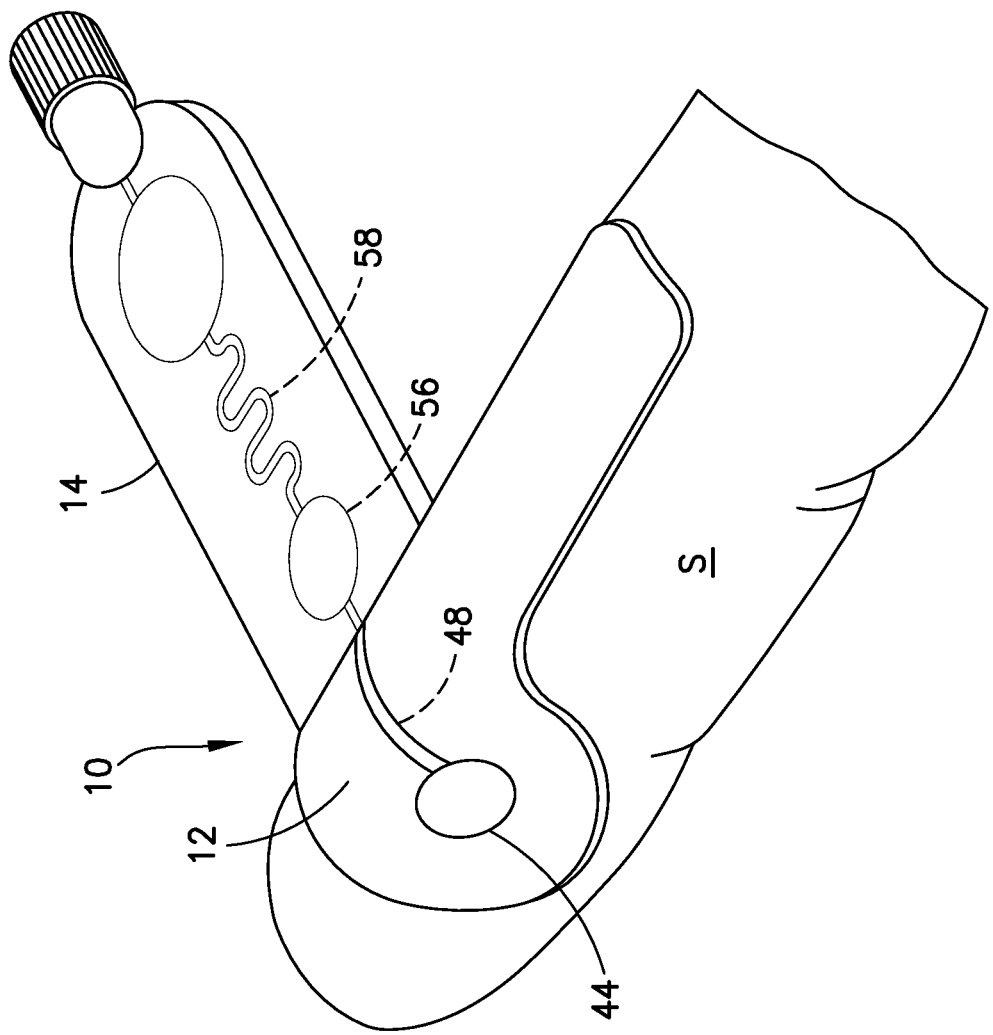
FIG. 11 is a perspective view of a blood sampling transfer device with a lancing tape secured to a patient in accordance with an embodiment of the present invention.

Referring to FIGS. 1-5, lancing tape 12 generally includes a longitudinal portion 40, a radial portion 42 extending from the longitudinal portion 40, a target or graphic indicator 44 on the radial portion 42, an inlet port 46 in fluid communication with the target 44, a lancing tape flow channel 48 integrally formed within the lancing tape 12 and in fluid communication with the inlet port 46, and an exit port 50 in fluid communication with the lancing tape flow channel 48 and a portion of the transfer cartridge 14 as will be described below. Referring to FIG. 1, the lancing tape 12 also includes a superior surface 45 and an inferior surface 47. The inferior surface 47 includes a mechanism for removably adhering the lancing tape 12 to a patient as shown in FIGS. 11 and 12.

In one embodiment, the inferior surface 47 includes an adhesive. The inferior surface 47 includes an adhesive so that the lancing tape 12 can be secured onto a skin surface S of a patient where a blood sample will be accessed. In one embodiment, the adhesive of the inferior surface 47 is protected by a peel-off layer, similar to an adhesive bandage, which would be removed before placing the lancing tape 12 on the skin surface S of the patient's body. A hydrogel or other layer (not shown) could be included to provide some thickness to the inferior surface 47 of the lancing tape 12 and help improve the stability of the adhesive seal. Additionally, in one embodiment, the adhesive could include a chemistry to create a more liquid-tight seal, similar to painter's tape technology, where wetting from the paint itself causes a chemical reaction with the adhesive to create a more water-tight barrier to prevent the paint from seeping under the tape. Importantly, the adhesive provides for proper adhesion of the lancing tape 12 to the skin surface S of a patient and minimizes skin contact which leads to a better sample for coagulation testing. The adhesive of the lancing tape 12 can be punctured by the lancet device 24 such that the blood evolving from the wound beneath passes through the cut into the lancing tape 12 to be collected inside the blood sampling transfer device 10. In one embodiment, the lancing tape 12 includes two layers, a bottom portion having an adhesive layer that is in contact with the skin and an upper portion that receives the evolving blood. The adhesive of the present disclosure includes an anti-leak mechanism. For example, in one embodiment, a self-sealing or self-healing polymer is used. In another embodiment, the top portion of the lancing tape 12 comprises a dome-shaped blister, which compresses under the lancet, but which pops back to its original shape after a lancing action thereby creating a space into which the blood will evolve, and then get wicked or moved by capillary action into the rest of the blood sampling transfer device 10. In another embodiment, the popping back to its original shape of the dome-shaped blister allows a vacuum force that helps pull the blood out of the wound.

Figure 2:
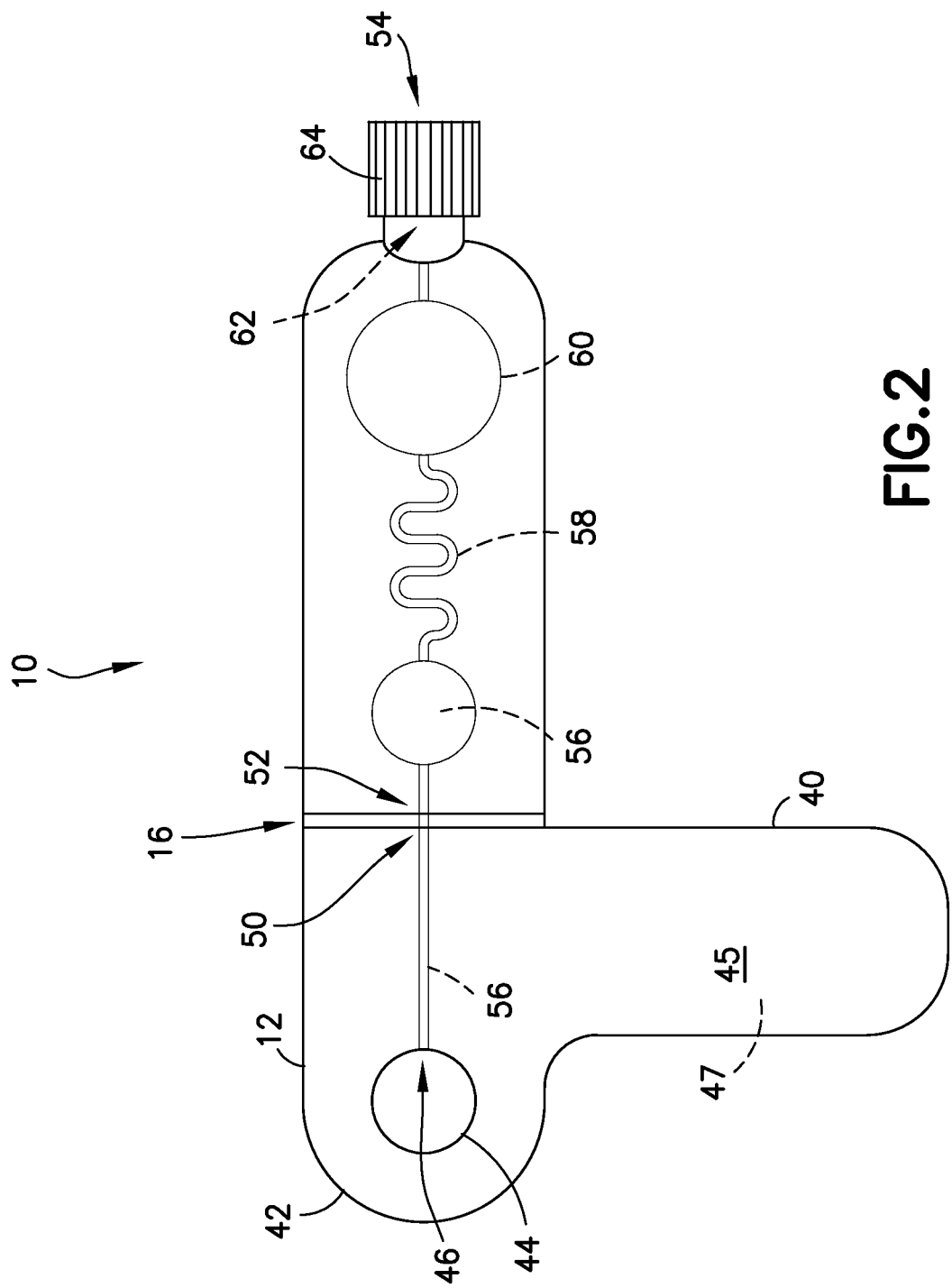
FIG. 2 is an elevation view of a blood sampling transfer device in accordance with an embodiment of the present invention.
Figure 3:
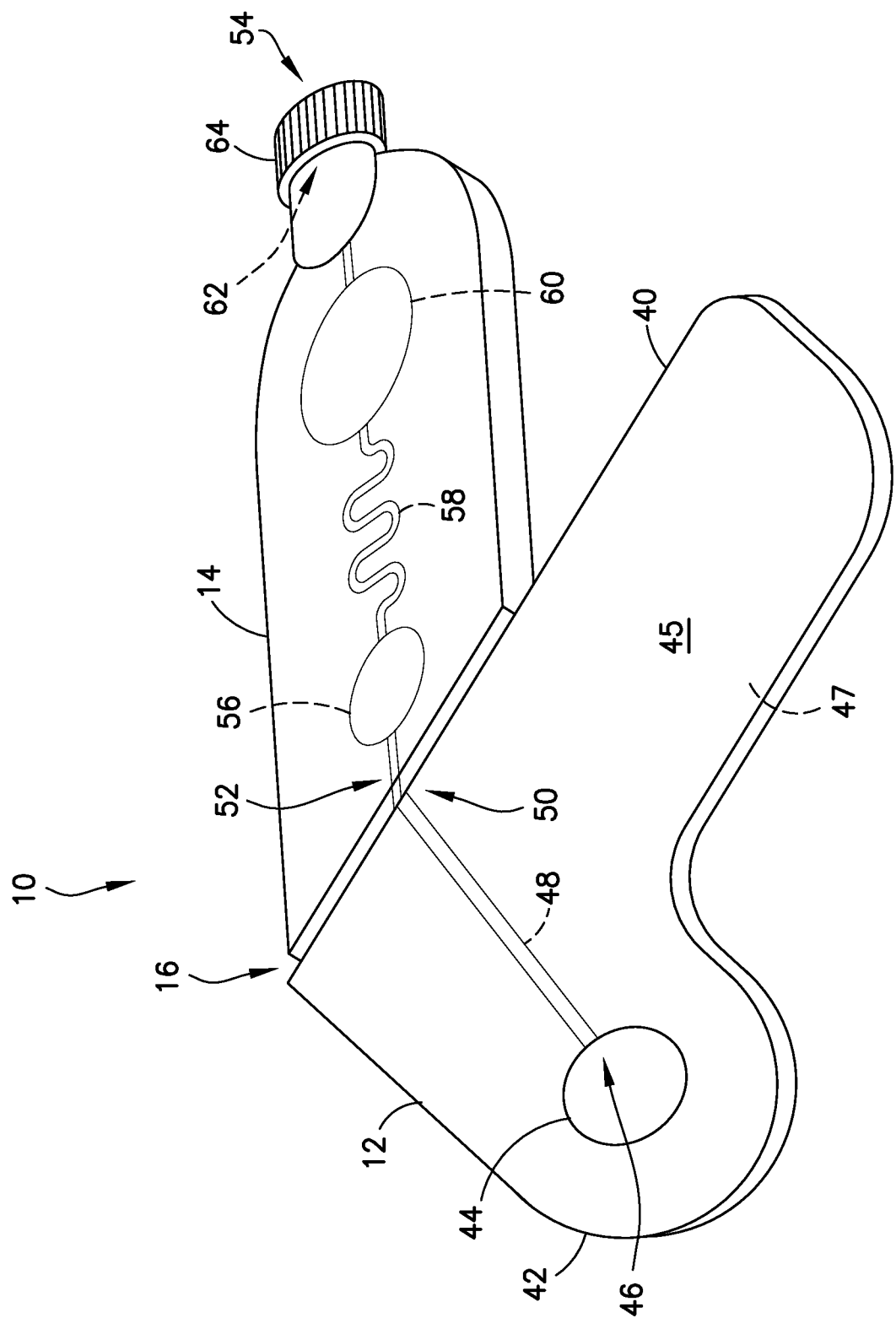
FIG. 3 is a perspective view of a blood sampling transfer device with a transfer cartridge being bent at a frangible portion in accordance with an embodiment of the present invention.
Figure 6:
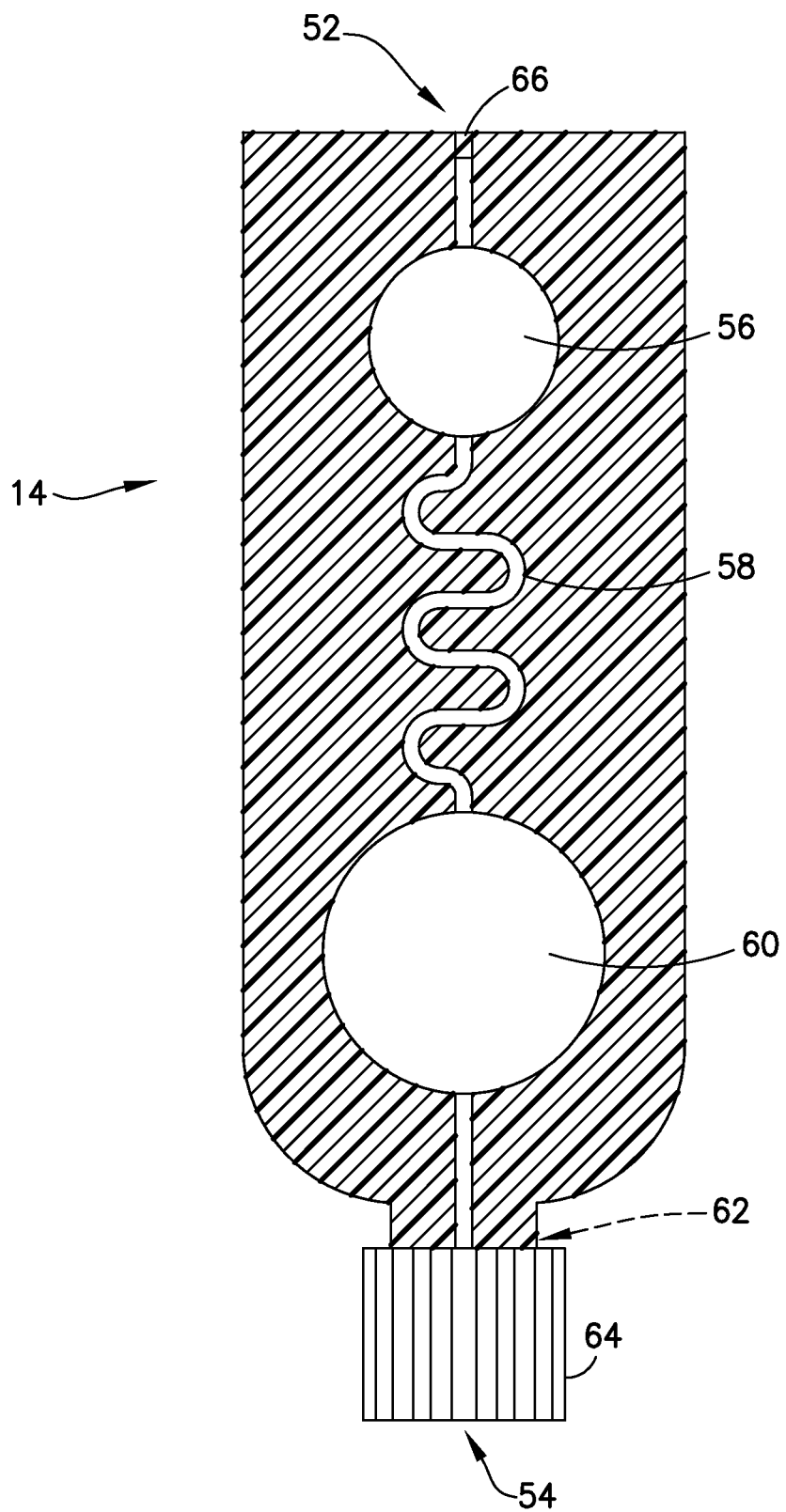
FIG. 6 is a cross-sectional view of the transfer cartridge of FIG. 5 in accordance with an embodiment of the present invention.
Figure 12:
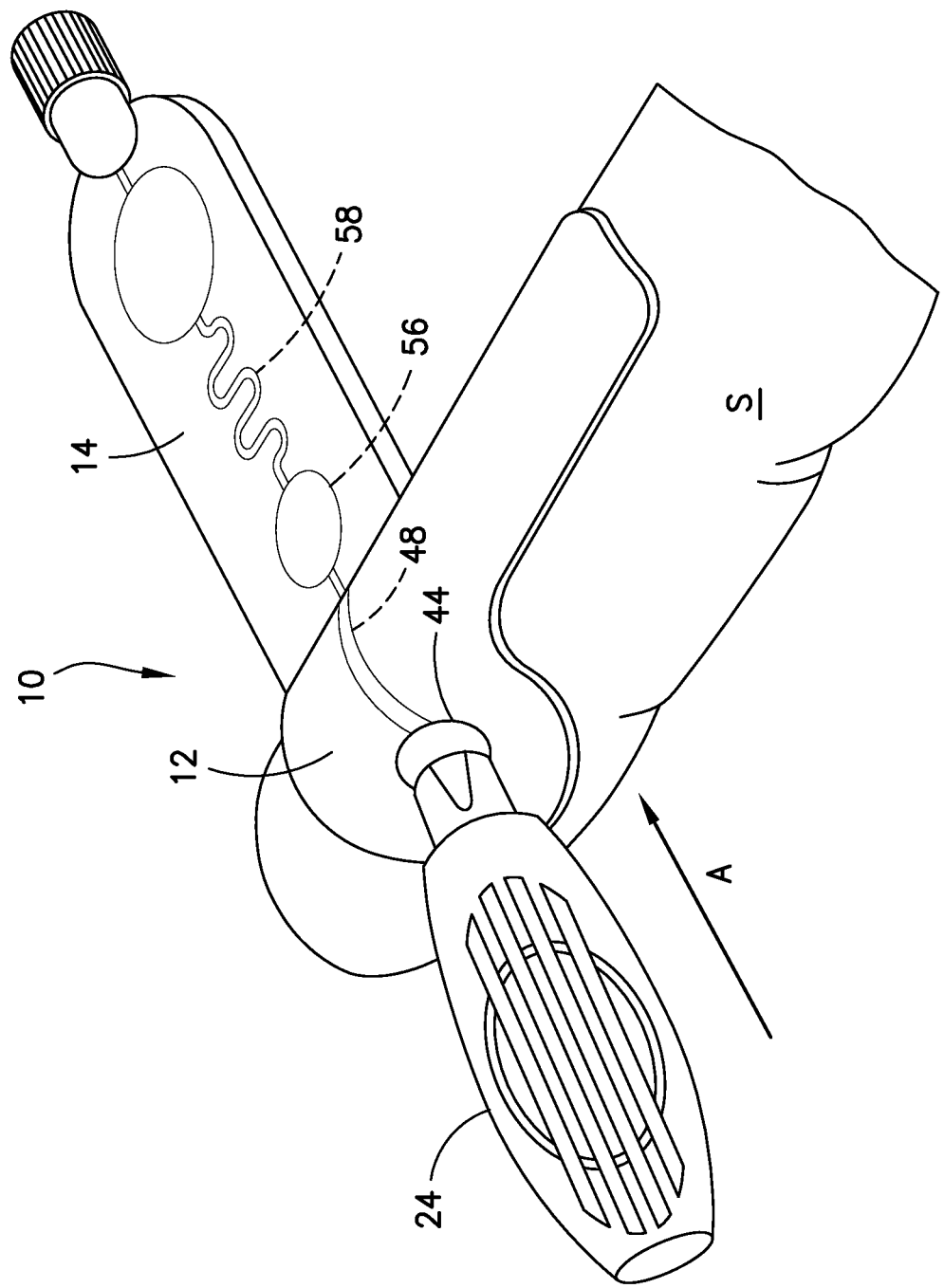
FIG. 12 is a perspective view of a blood sampling transfer device with a lancing tape secured to a patient and a lancet device aligned with the lancing tape in accordance with an embodiment of the present invention.

The target 44 of the lancing tape 12 provides an alignment and targeting mechanism for the lancet device 24 as shown in FIG. 12. In one embodiment, the target 44 comprises a circular shape. In other embodiments, the target 44 can have other multi-sided polygon cross-sectional shapes, such as square or rectangular cross-sectional shapes. As shown in FIGS. 1 and 2, the target 44 of the lancing tape 12 is aligned with and in fluid communication with the inlet port 46 and the lancing tape flow channel 48.

Referring to FIGS. 1-6, transfer cartridge 14 generally includes an inlet port 52 in fluid communication with the exit port 50 of the lancing tape 12, an entry reservoir 56 in fluid communication with the inlet port 52, a transfer cartridge flow channel 58 in fluid communication with the entry reservoir 56, an exit reservoir or dispensing bulb 60 in fluid communication with the transfer cartridge flow channel 58, an exit port 54 in fluid communication with the exit reservoir 60, a valve 62 disposed in communication with the exit port 54, and an end cap 64. The transfer cartridge 14 is adapted to contain a sample stabilizer to provide passive and fast mixing of a blood sample with the sample stabilizer. The sample stabilizer can be an anticoagulant, or a substance designed to preserve a specific element within the blood such as, for example, RNA, protein analyte, or other element. In one embodiment, the sample stabilizer is provided within the transfer cartridge flow channel 58. In other embodiments, the sample stabilizer is provided in other areas of the transfer cartridge 14 such as the inlet port 52 or the entry reservoir 56.

Figure 14:
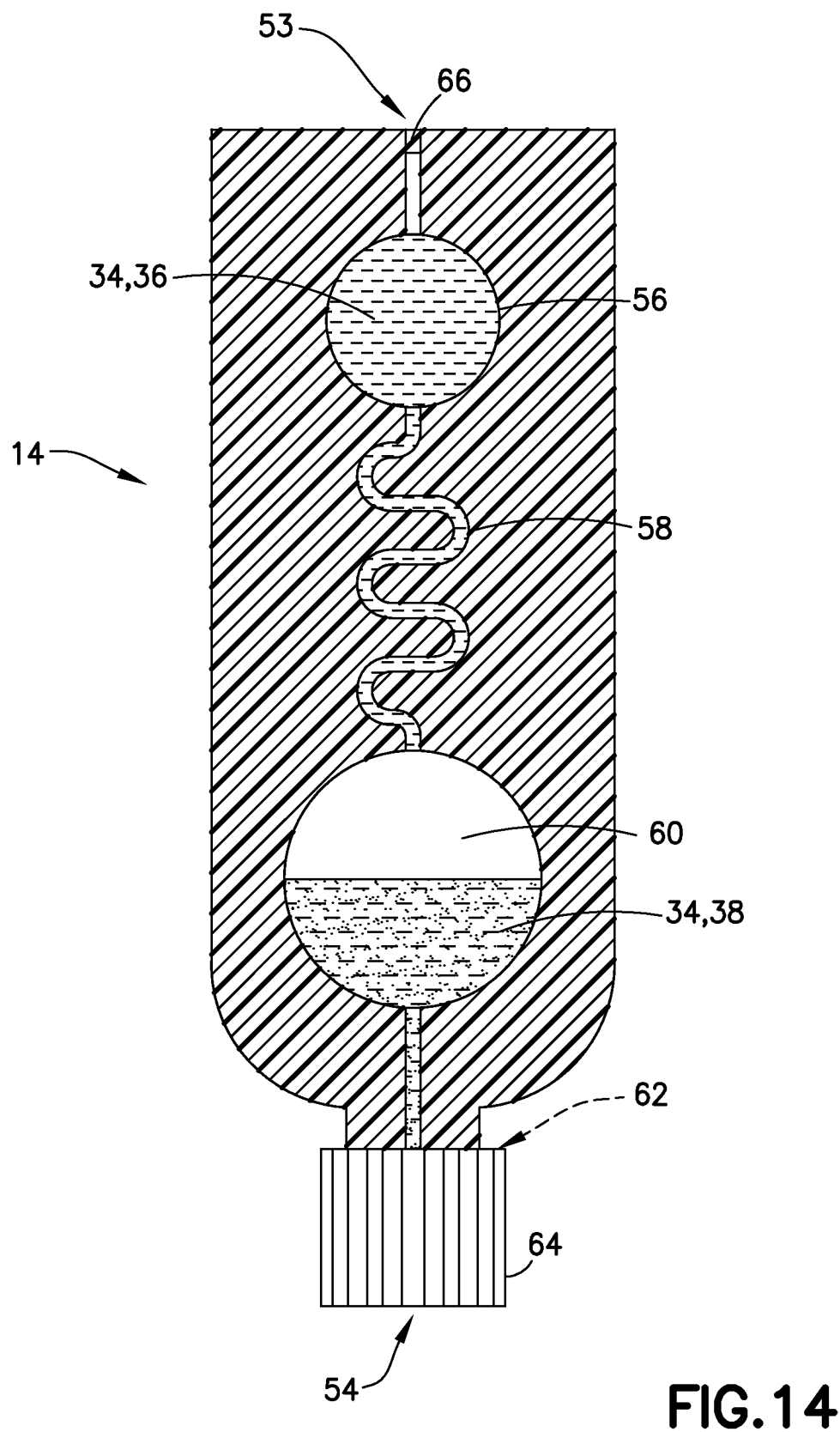
FIG. 14 is a cross-sectional view of the transfer cartridge of FIG. 5 in accordance with an embodiment of the present invention.
Figure 16:
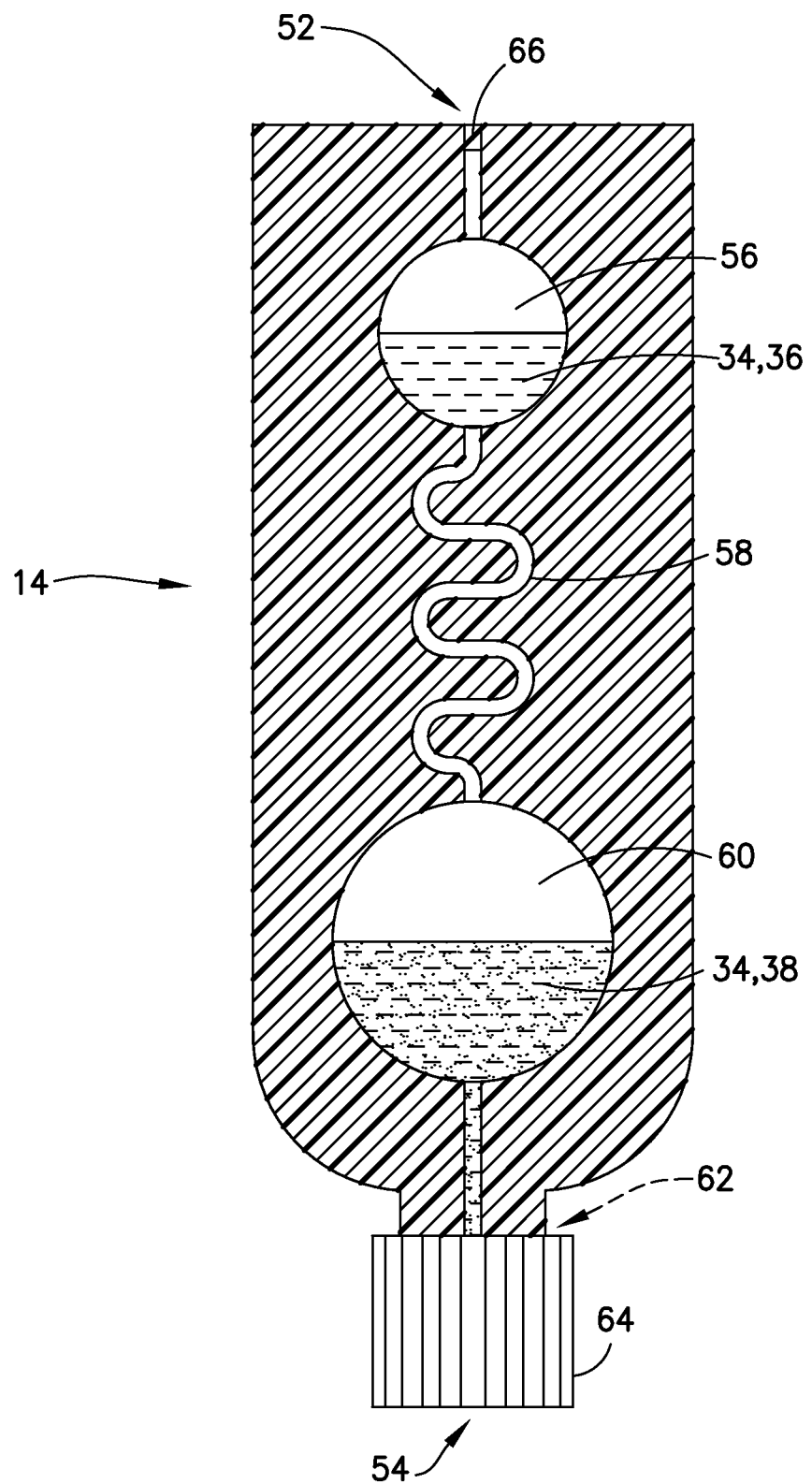
FIG. 16 is a cross-sectional view of the transfer cartridge of FIG. 5 in accordance with an embodiment of the present invention.

In one embodiment, the transfer cartridge flow channel 58 comprises a serpentine shape to promote efficient mixing of a blood sample 34 (FIGS. 14 and 16) having a cellular portion 36 and a plasma portion 38. As discussed below, a centrifuge 32 provides a rotational force applied to the transfer cartridge 14 to separate the plasma portion 38 from the cellular portion 36 through the transfer cartridge flow channel 58. In other embodiments, the transfer cartridge flow channel 58 comprises other shapes to promote efficient mixing of a blood sample.

Figure 17:
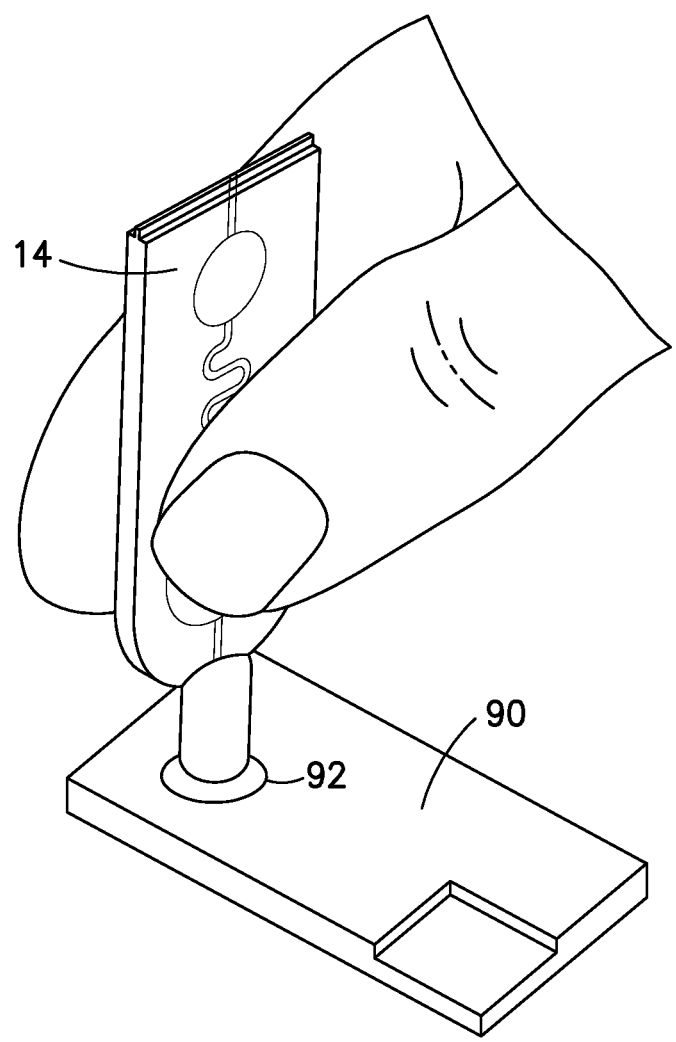
FIG. 17 is a perspective view of a transfer cartridge and a point-of-care testing device in accordance with an embodiment of the present invention.

The valve 62 is transitionable between a closed position to seal a plasma portion within the exit reservoir 60 of the transfer cartridge and an open position to allow a plasma portion to flow through the exit port 54 and the end cap 64 to a point-of-care testing device 90 as shown in FIG. 17.

Referring to FIGS. 1-5, the transfer cartridge 14 is removably connected to the lancing tape 12 via a frangible element or frangible portion 16. With the transfer cartridge 14 connected to the lancing tape 12, the entry reservoir 56 and inlet port 52 of the transfer cartridge 14 are in fluid communication with the lancing tape flow channel 48 and exit port 50 of the lancing tape 12. The frangible element 16 includes a frangible element sealing wall 66. Referring to FIG. 5, after the frangible element 16 is broken to remove the transfer cartridge 14 from the lancing tape 12, the frangible element sealing wall 66 seals the inlet port 52 of the transfer cartridge 14. After the frangible element 16 is broken to remove the transfer cartridge 14 from the lancing tape 12, the exit port 50 of the lancing tape 12 is also sealed to seal the lancing tape flow channel 48.

Referring to FIG. 10, a blood sampling system 20 of the present disclosure includes a kit 22 having a lancet device 24, a blood sampling transfer device 10 having a lancing tape 12 having a flow channel 48 and a transfer cartridge 14 removably connected to the lancing tape 12, and a packaging member 26 having a compartment 68 sized and adapted to receive the lancet device 24 and the blood sampling transfer device 10 therein. The packaging member 26 includes a body or wall defining a compartment 68. In one embodiment, the body of the packaging member 26 defines a first compartment 70 sized and adapted to receive the blood sampling transfer device 10 therein and a second compartment 72 sized and adapted to receive the lancet device 24 therein. In one embodiment, the packaging member 26 comprises a blister package. In one embodiment, a sealing cover is secured over the packaging member 26 to seal the blood and sampling transfer device 10 and the lancet device 24 therein, i.e., the sealing cover provides a substantially impermeable enclosure with respect to packaging member 26, provides a leak prevention and protection enclosure, protects the contents of the blood and sampling transfer device 10 and the lancet device 24 contained within packaging member 26, and/or maintains a sealed, sterilized environment within packaging member 26. The sealing cover of the packaging member 26 provides a sufficient seal at a range of temperatures, pressures, and humidity levels. In one embodiment, tamper evidence is also provided by use of a tear strip or other indicating means secured to a portion of the sealing cover and/or packaging member 26 to indicate tampering with the contents of packaging member 26.

Referring to FIGS. 7, 8, 9, 12, and 13, a lancet device 24 of the present disclosure is shown. In one embodiment, the lancet device 24 may be a contact activated lancet device. In other embodiments, the lancet device 24 may be any type of lancet device. In another embodiment, the lancet device 24 may be sized to be contained within a target 44 or dome of the lancing tape 12. In this manner, a user could push down on the target 44 to activate the lancet and pierce the skin of a patient.

In one embodiment, the lancet device 24 generally includes a housing 100, a shield 102 movably associated with the housing 100, and a lancet structure 104 disposed therein. As will be discussed below, the shield 102 is coaxially and movably associated with the housing 100, and is partially disposed within the housing 100, extending partially outward from the housing 100, with the lancet structure 104 contained within and axially or longitudinally movable through the shield 102. The lancet structure 104 includes a puncturing element 106, the lancet structure 104 at least partially disposed within the housing 100 and adapted for movement between a pre-actuated position (FIG. 9) wherein the puncturing element 106 is retained within the housing 100 and a puncturing position (FIG. 13) wherein at least a portion of the puncturing element 106 extends through a forward end 110 of the housing 100.

The housing 100 defines an elongated body, and is desirably formed with a main body 112 defining a distal or forward end 110, and a rear cap 114 defining a proximal or rearward end 116. The interior portion of housing 100 is generally open defining an internal cavity 118, the internal cavity 118 is closed at the rearward end 116 through rear cap 114 and includes an opening 120 through the forward end 110, through which the shield 102 extends. Main body 112 and rear cap 114 may be integrally formed. Alternatively, main body 112 and rear cap 114 are separate elements which are affixed to each other to form housing 100, which aids in assembly of the lancet device 24. Main body 112 and rear cap 114 may be affixed together through an appropriate adhesive, or may include inter-engaging structure providing a mechanical attachment therebetween, such as a frictional fit or a snap fit construction. In an alternate embodiment, main body 112 and rear cap 114 may be an integrally formed structure, and may therefore be molded together as one component.

Figure 7:
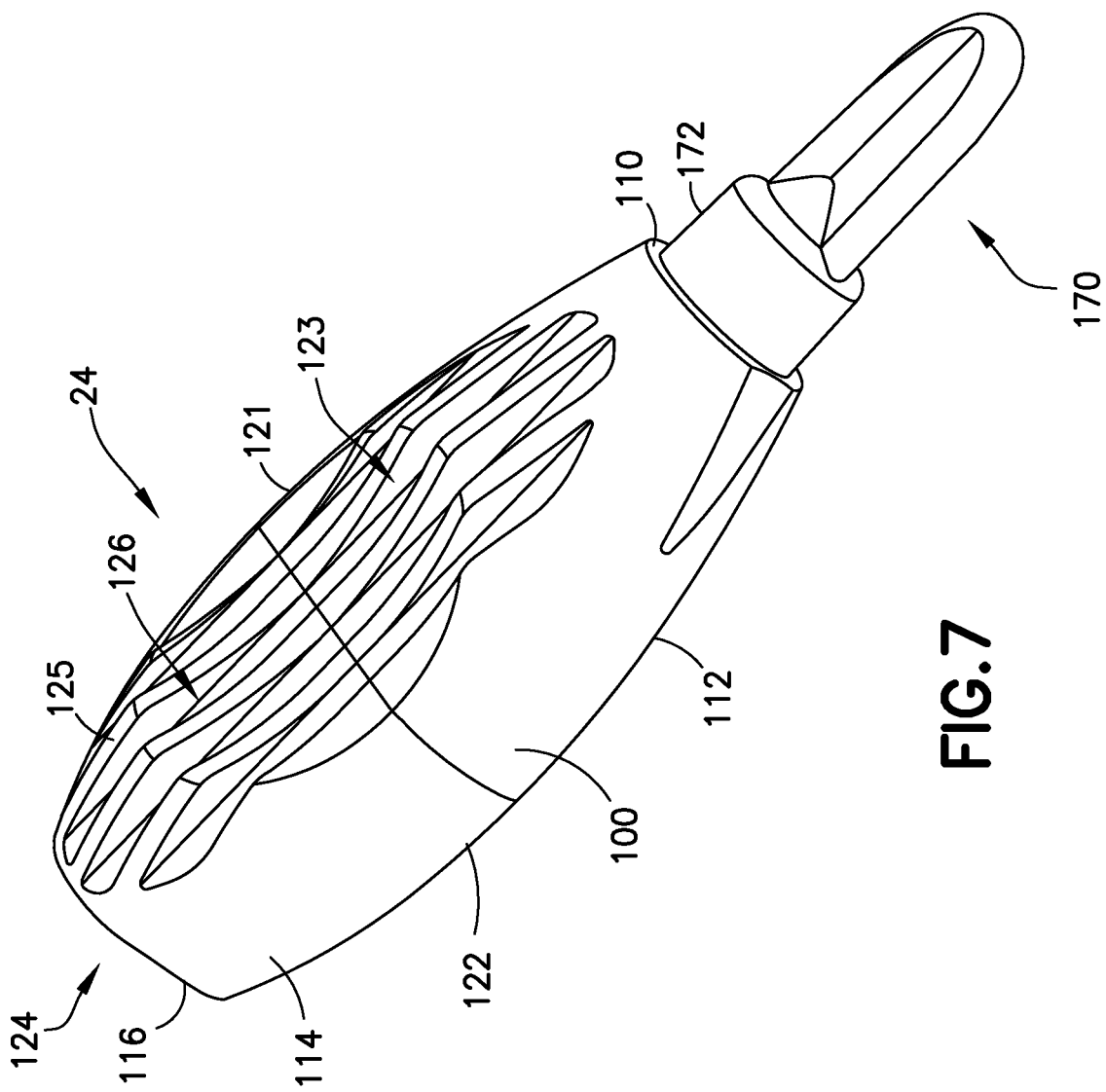
FIG. 7 is a perspective view of a lancet device in accordance with an embodiment of the present invention.
Figure 8:
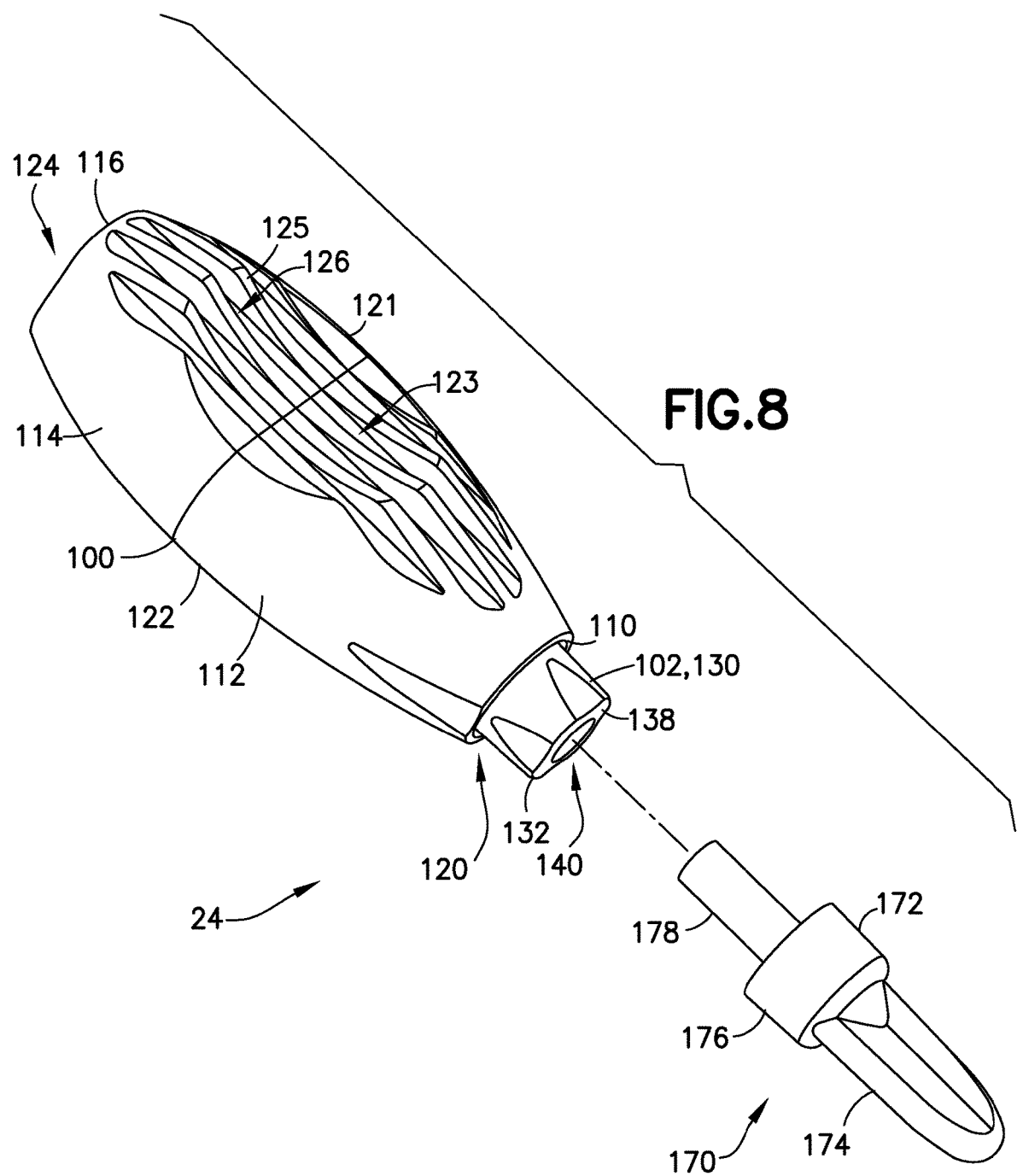
FIG. 8 is an exploded, perspective view of a lancet device in accordance with an embodiment of the present invention.

As shown in FIGS. 7 and 8, the housing 100, defined by main body 112 and rear cap 114, has opposed sides 121, 122, which may each include a surface for accommodating a user's fingers, such as finger grip indentations 123, which may be formed as a concave depression or recess. While two opposed finger grip indentations 123 may be provided on the housing 100, it will be appreciated that only one finger grip indentation 123 formed in the housing 100 may be provided in accordance with the present invention. Additionally, the rearward end 116 of housing 100, such as the top surface of rear cap 114, may also include a surface for accommodating a user's finger, such as a rear finger grip indentation 124, which may also be formed as a concave depression or recess. The side finger grip indentations 123 and the rear finger grip indentation 124 provide ergonomically shaped surfaces that substantially conform to a user's fingertips to aid the user in manipulating the lancet device 24 and using the lancet device 24 in a blood letting, drawing, or collection procedure, and may provide multiple finger grip positions for the user. In one embodiment, the housing 100 may further include structure to generally improve the grip between the housing 100 and the user's fingertips, such as a plurality of longitudinal ribs 125 and troughs 126 extending along the housing 100 and integrally formed with the housing 100, which may provide a visual and tactile cue to the user to instruct the user where to place his or her fingertips.

Figure 9:
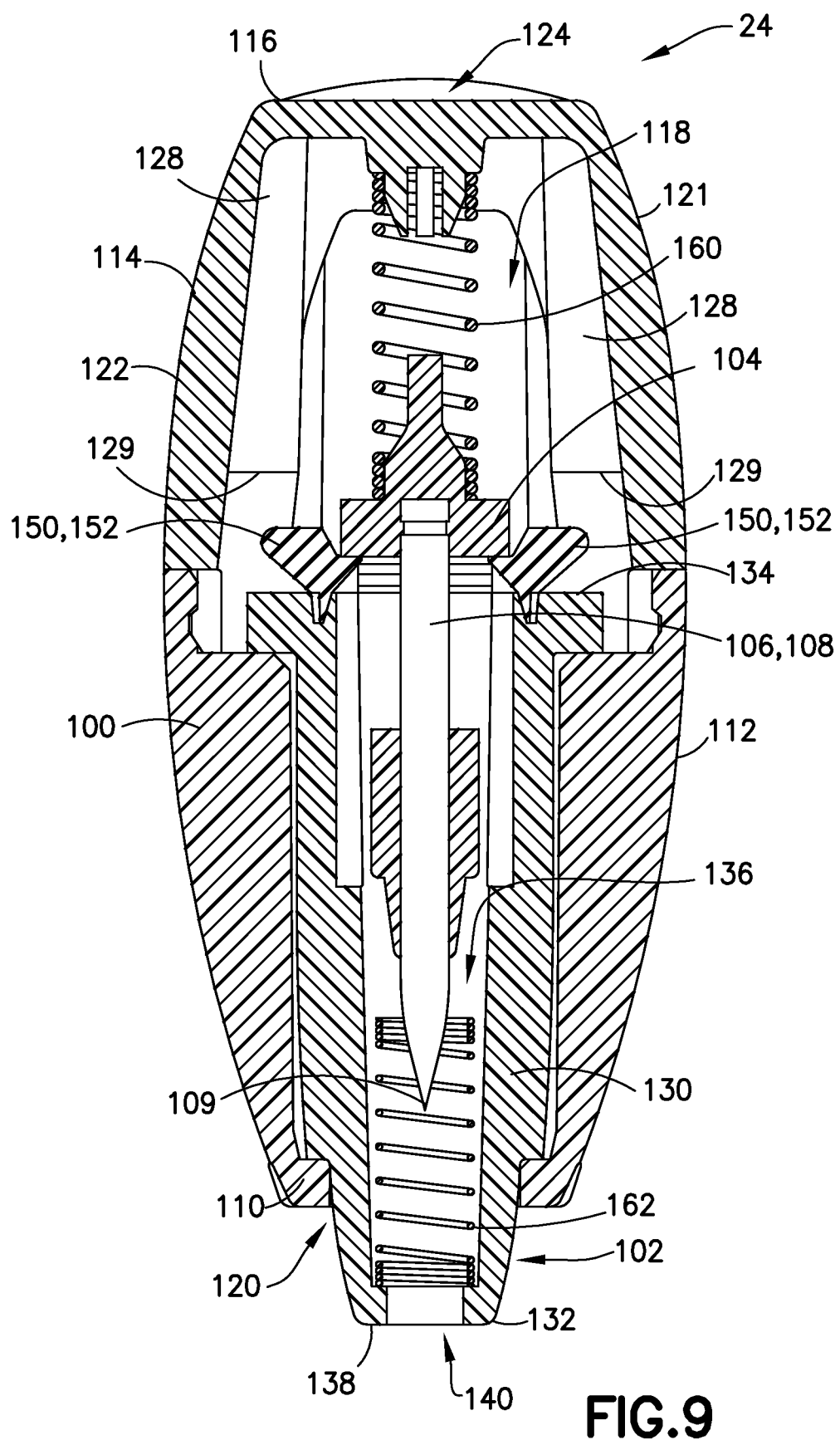
FIG. 9 is a cross-sectional view of the lancet device of FIG. 8 in accordance with an embodiment of the present invention.
Figure 13:
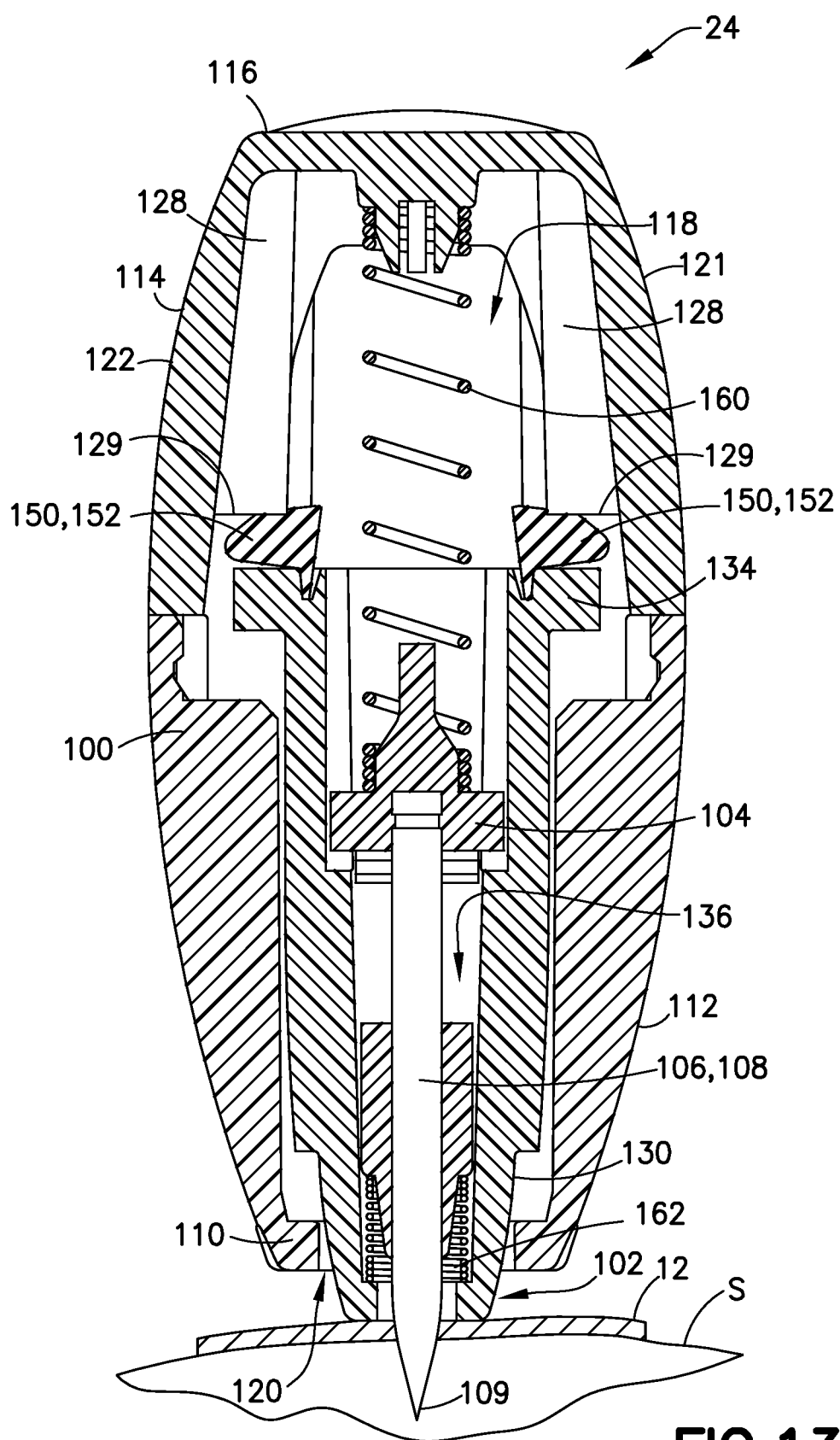
FIG. 13 is a cross-sectional view of the lancet device and the lancing tape secured to a patient in accordance with an embodiment of the present invention.

The shield 102 extends outward from the opening 120 through the forward end 110 of the housing 100. As shown in FIGS. 9 and 13, the shield 102 is a generally cylindrical hollow structure having a shield body 130 extending between a forward end 132 and a rearward end 134, and defining an internal cavity 136 extending therethrough. The forward end 132 of the shield body 130 defines a forward end wall 138 including a forward opening 140 therethrough, through which the puncturing element 106 of the lancet structure 104 extends when the lancet device 24 is actuated by the user. The forward end wall 138 generally defines a small contact area about the opening 140 for contacting the intended area on the user's body which is to be punctured by the puncturing element. The shield 102 is axially or longitudinally movable within the housing 100. The shield 102 and housing 100 may include corresponding guiding surfaces for guiding the shield 102 through the housing 100.

Lancet device 24 further includes a lancet structure 104 disposed within the housing 100, and extending through shield 102. As shown in FIGS. 9 and 13, lancet structure 104 includes a puncturing element 106, shown in the form of lancet 108 defining a puncturing end 109 at the forward end thereof. Lancet structure 104 is adapted for axial or longitudinal movement through the internal cavity 136 of the shield body 130 between an initial armed or pre-actuated position with the puncturing end 109 maintained within the shield body 130 to a puncturing position in which the puncturing end 109 extends beyond the forward opening 140 of shield body 130. Puncturing end 109 is adapted for puncturing the skin of a patient, and may define a pointed end, a blade edge, and the like. Puncturing end 109 may include a preferred alignment orientation, such as with a pointed end of a blade aligned in a specific orientation.

As shown in FIGS. 9 and 13, a retaining hub 150 is provided at the rearward end 134 of the shield body 130. Retaining hub 150 is provided as a separate structure disposed or retained within the rearward end 134 of shield body 130. In one embodiment, shield body 130 may include a surface for supporting and positioning retaining hub 150 to assist in assembly. In another embodiment, the retaining hub 150 may be molded or formed directly onto the shield body 130.

Retaining hub 150 defines a lever structure 152 for retaining the lancet structure 104 in an initial armed position retracted within housing 100 as shown in FIG. 9. Retaining hub 150 and lancet structure 104 are in interference engagement with each other, such that retaining hub 150 retains the lancet structure 104 in an initial armed position retracted within housing 100.

Moreover, the lever element 152 is adapted for contacting engagement with a structure defined within housing 100. For example, rear cap 114 of housing 100 may include structure extending therein, such as an internal contact 128 integrally formed and extending on at least one, and desirably on two opposing inner sidewalls thereof as shown in FIGS. 9 and 13. Each internal contact 128 includes an engagement surface 129 for contacting engagement with a contact surface of lever element 152, forming a cam surface. In this manner, the pair of internal contacts 128 may engage the lever elements 152, thereby providing a continual cam-like contact surface during pivotal movement of lever element 152.

Movement of the lancet structure 104 through the lancet device 24 is achieved through a biasing force provided through a drive spring 160. Drive spring 160 is adapted to exert a biasing force against lancet structure 104 to drive lancet structure 104 through the device toward the puncturing position, and may be disposed between the rearward end of the housing 100 and the lancet structure 104. When the lancet structure 104 is in an armed position, the drive spring 160 exerts a force against the lancet structure, such as between the rearward end of housing 100 and the lancet structure 104, biasing the lancet structure 104 toward the puncturing position.

Referring to FIGS. 9 and 13, a retraction spring 162 may be provided at the forward end of the lancet device 24, for retracting the lancet structure 104 within the shield body 130 after the lancet structure 104 is axially moved to the puncturing position. The retraction spring 162 extends between a forward surface of the lancet structure 104 and an inner surface within the forward end wall 138 of the shield body 130. Retraction spring 162 is typically a compression spring, capable of storing energy when in a compressed state.

Referring to FIGS. 7 and 8, lancet device 24 may further include a protective cover 170 for protectively covering the lancet device 24 prior to use thereof. The protective cover 170 may include a tab member 172 associated with the forward end of the lancet device 24, which maintains sterility of the forward end wall 138 of shield body 130. The tab member 172 may include a forward tab portion 174 and a depending skirt 176. The depending skirt 176 is adapted to cooperate with the forward end 132 of the shield body 130, generally encompassing or enclosing the forward end 132. The depending skirt 176 also contacts the forward end 110 of the main body 112 of the housing 100. In this manner, the tab member 172 encloses forward opening 120 of main body 112 and forward opening 140 of shield body 130. Moreover, such arrangement maintains the respective forward ends of main body 112 and shield body 130 in fixed relation with respect to each other, thereby preventing movement therebetween which could cause premature activation of the lancet device 24. In one embodiment, a post portion 178 of the protective cover 170 may extend within the shield body 130 to encompass at least a portion of the puncturing element 106.

The respective elements of the lancet device of the present invention are all typically formed of molded plastic material, such as a medical grade plastic material. The lancet 108 may be constructed of any suitable material adapted for puncturing the skin, and is typically a surgical grade metal such as stainless steel.

Referring to FIGS. 7-9 and 13, use of the lancet device 24 will now be described. To prepare the lancet assembly for use, the user grasps the housing 100, such as between a finger and thumb on opposing sides 121, 122, and removes the protective cover 170 from the forward end as shown in FIG. 8, thereby exposing the shield body 130 extending from the forward end of main body 112 of housing 100. The forward end wall 138 of shield body 130 may then be contacted with a location on the user's body or another person's body where it is desired to initiate blood flow, such as the patient's skin surface S as shown in FIGS. 11-13.

Once placed against the body, the user exerts a downwardly directed force on the housing 100 forcing shield body 130 against skin surface S. Since retaining hub 150 is adjacent rearward end 134 of shield body 130, such displacement of the shield body 130 toward the rear cap 114 causes corresponding rearward movement of retaining hub 150 toward rear cap 114. Such movement causes drive spring 160 to compress. This compressing of drive spring 160 arms drive spring 160 with a biasing force sufficient to propel lancet structure 104 axially forward through shield body 130 to the puncturing position, thereby providing lancet structure 104 in an armed position. At this point, however, lancet structure 104 is still maintained such that puncturing end 109 is retracted within shield body 130 due to the interference engagement between the retaining hub 150 and the lancet structure 104.

Such rearward movement of retaining hub 150 causes the cam surfaces of engagement surfaces 129 of the internal contacts 128 within rear cap 114 to engage and co-act with the corresponding contact surfaces of the lever elements 152. Accordingly, the corresponding camming contact surfaces provide an actuator element for the lancet device 24. Such engagement and co-action causes the lever elements 152 to pivot to release the lancet structure 104 through the shield body 130. Eventually, such pivoting causes the lever elements 152 to be pivoted to a point at which the interference engagement between the retaining hub 150 and the lancet structure 104 is released, as shown in FIG. 13. The biasing force of drive spring 160 propels lancet structure 104 downward away from the rear cap 114 axially through housing 100 and shield body 130.

Referring to FIG. 15, a blood separation system 30 of the present disclosure for a blood sample 34 (FIGS. 14 and 16) having a cellular portion 36 and a plasma portion 38 includes a blood sampling transfer device 10 adapted to receive a blood sample and having a lancing tape 12 having a flow channel 48 and a transfer cartridge 14 removably connected to the lancing tape 12, and a centrifuge 32 having a receiving port 74 adapted to receive the transfer cartridge 14 such that with the transfer cartridge 14 received within the centrifuge 32 and a rotational force applied to the transfer cartridge 14, a plasma portion of the blood sample is separated from a cellular portion. The centrifuge 32 includes a plurality of receiving ports 74 adapted to receive a transfer cartridge 14, a base or bottom portion 78, a top portion 76 movably connected to the base portion 78 by a hinged portion 80, and a rotational force element 82 contained within the base portion 78. The top portion 76 is transitionable between an open position in which a transfer cartridge 14 can be placed within a receiving port 74 as shown in FIG. 15 and a closed position. With the transfer cartridge 14 received within the centrifuge 32, a rotational force is applied to the transfer cartridge 14 to separate the plasma portion 38 from the cellular portion 36 as described in more detail below.

Referring to FIGS. 10-17, use of a blood sampling transfer device of the present disclosure will now be described. Referring to FIGS. 10-12, upon selecting a site, a clinician removes the lancing tape 12 with the transfer cartridge 14 connected thereto from the packaging member 26. The clinician then adheres the lancing tape 12 over a selected sampling site as shown in FIGS. 11 and 12. A target for a lancet device 24 is highlighted with the target 44 provided on the lancing tape 12. The clinician then places a tip of the lancet device 24 onto the target 44 and pushes against the site in the direction of arrow A to activate the lancet device 24 and puncture the skin S. The target 44 corresponds to the integrated flow through channel 48 to carry blood through the lancing tape flow channel 48 of the lancing tape 12 and into the entry reservoir 56 of the transfer cartridge 14 via capillary action. The transfer cartridge 14 contains anticoagulant within a serpentine (or other) flow channel 58 to promote efficient mixing of specimen. When the entry reservoir 56 of the transfer cartridge 14 is filled, the clinician can snap off the frangible element 16 between the lancing tape 12 and the transfer cartridge 14. When broken away, the flow channel 58 of the transfer cartridge 14 is sealed from the external environment.

Referring to FIG. 15, the next step of the process involves manual insertion into a point-of-care centrifuge device 32 designed specifically for the transfer cartridge 14. The blood is quickly spun and due to the low volume is separated within a few seconds such that the plasma portion 38 is collected within a dispensing bulb 60 of the transfer cartridge 14. The transfer cartridge 14 is removed manually from the centrifuge device 32. Thereafter, referring to FIG. 17, the plasma portion of the blood sample within the dispensing bulb 60 of the transfer cartridge 14 is dispensed through the exit port 54 of the transfer cartridge 14 by squeezing the dispensing bulb 60 into a well or receiving port 92 of the point-of-care testing device 90 to perform the desired test. The dispensing bulb 60 has a valve 62 to avoid leaking until the bulb 60 is depressed as discussed above. The transfer cartridge 14 can then be disposed of or can be retained for additional testing procedures. In addition, bar code labels or RFID tags that can be read by the centrifuge device 32 may be provided on the transfer cartridge 14 to provide various information to the system.

Some of the advantages of the present disclosure over prior systems are that it is a closed system which reduces sample exposure, it provides passive and fast mixing of the sample with an anti-coagulant, it facilitates separation of the sample without transferring the sample, and it is capable of transferring pure plasma to the point-of-care testing device 90.

The blood sampling transfer device of the present disclosure may also be used to transfer a blood sample to a point-of-care testing device that uses the whole blood sample as an input. Not every application of the blood sampling transfer device of the present disclosure would require that plasma be created by centrifugation.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A blood sampling transfer device, comprising:
an adhesive lancing tape having a target, and a flow channel in fluid communication with a portion of the target;
a transfer cartridge removably connected to the lancing tape, the transfer cartridge having a reservoir, wherein the adhesive lancing tape and the transfer cartridge are positioned in the same horizontal plane relative to one another, and
a frangible portion integrally formed between the transfer cartridge and the lancing tape such that the transfer cartridge and the lancing tape are detachably connected to one another via the frangible portion, the frangible portion including a sealing wall, the sealing wall configured such that upon breaking of the frangible portion to remove the transfer cartridge from the lancing tape, the sealing wall seals the reservoir, and wherein an inlet of the reservoir connected to the frangible portion is laterally offset from the target relative to a puncture direction of a puncturing element into the target, wherein the flow channel is configured to permit a blood sample to flow from the target and through the frangible portion before entering the transfer cartridge, wherein, in a first position when the transfer cartridge is connected to the lancing tape, the reservoir is configured to be in fluid communication with the flow channel, and wherein, in a second position when the transfer cartridge is disconnected from the lancing tape, the transfer cartridge is configured to be separated from the lancing tape.

2. The blood sampling transfer device of claim 1, wherein the target of the lancing tape is aligned with the flow channel to promote flow of the blood sample via capillary action.

3. The blood sampling transfer device of claim 1, wherein the target of the lancing tape is a circular graphic indicator.

4. The blood sampling transfer device of claim 1, wherein the transfer cartridge includes a transfer cartridge flow channel in fluid communication with the reservoir.

5. The blood sampling transfer device of claim 4, wherein the transfer cartridge flow channel comprises a sample stabilizer and the transfer cartridge flow channel is configured to allow for passive mixing of the sample with the sample stabilizer.

6. The blood sampling transfer device of claim 4, wherein the transfer cartridge includes a dispensing bulb in fluid communication with the transfer cartridge flow channel, the transfer cartridge flow channel disposed between the dispensing bulb and the reservoir.

7. A blood sampling system, comprising:
a lancet device having a lancet; and
a blood sampling transfer device, comprising:
an adhesive lancing tape having a target, and a flow channel in fluid communication with a portion of the target;
a transfer cartridge removably connected to the lancing tape, the transfer cartridge having a reservoir, wherein the adhesive lancing tape and the transfer cartridge are positioned in the same horizontal plane relative to one another, and
a frangible portion integrally formed between the transfer cartridge and the lancing tape such that the transfer cartridge and the lancing tape are detachably connected to one another via the frangible portion, the frangible portion including a sealing wall, the sealing configured such that upon breaking of the frangible portion to remove the transfer cartridge from the lancing tape, the sealing wall seals the reservoir, and wherein an inlet of the reservoir connected to the frangible portion is laterally offset from the target relative to a puncture direction of the lancet into the target,
wherein the flow channel is configured to permit a blood sample to flow from the target and through the frangible portion before entering the transfer cartridge,
wherein, in a first position when the transfer cartridge is connected to the lancing tape, the reservoir is configured to be in fluid communication with the flow channel, and
wherein, in a second position when the transfer cartridge is disconnected from the lancing tape, the transfer cartridge is configured to be separated from the lancing tape.

8. The blood sampling system of claim 7, wherein the target of the lancing tape is a circular graphic indicator.

9. The blood sampling system of claim 7, wherein the transfer cartridge includes a transfer cartridge flow channel in fluid communication with the reservoir to promote passive movement of the blood sample through the transfer cartridge flow channel via capillary action.

10. The blood sampling system of claim 9, wherein the transfer cartridge flow channel comprises a sample stabilizer and the transfer cartridge flow channel is configured to allow for passive mixing of the sample with the sample stabilizer.

11. The blood sampling system of claim 9, wherein the transfer cartridge includes a dispensing bulb in fluid communication with the transfer cartridge flow channel, the transfer cartridge flow channel disposed between the dispensing bulb and the reservoir.

12. A blood sampling system, comprising:
a lancet device having a lancet;
a blood sampling transfer device, comprising:
an adhesive lancing tape having a target, and a flow channel in fluid communication with a portion of the target;
a transfer cartridge removably connected to the lancing tape, the transfer cartridge having a reservoir, wherein the adhesive lancing tape and the transfer cartridge are positioned in the same horizontal plane relative to one another, and
a frangible portion integrally formed between the transfer cartridge and the lancing tape such that the transfer cartridge and the lancing tape are detachably connected to one another via the frangible portion, the frangible portion including a sealing wall, the sealing configured such that upon breaking of the frangible portion to remove the transfer cartridge from the lancing tape, the sealing wall seals the reservoir, and wherein an inlet of the reservoir connected to the frangible portion is laterally offset from the target relative to a puncture direction of the lancet into the target,
wherein the flow channel is configured to permit a blood sample to flow from the target and through the frangible portion before entering the transfer cartridge,
wherein, in a first position when the transfer cartridge is connected to the lancing tape, the reservoir is configured to be in fluid communication with the flow channel, and
wherein, in a second position when the transfer cartridge is disconnected from the lancing tape, the transfer cartridge is configured to be separated from the lancing tape; and
a packaging member having a compartment sized and adapted to receive the lancet device and the blood sampling transfer device therein.

13. The blood sampling system of claim 12, wherein the lancing tape includes the adhesive on an inferior surface of the lancing tape.

14. A blood separation system for a blood sample having a cellular portion and a plasma portion, the blood separation system comprising:
a blood sampling transfer device adapted to receive the blood sample, the blood sampling transfer device comprising:
an adhesive lancing tape having a target, and a flow channel in fluid communication with a portion of the target;
a transfer cartridge removably connected to the lancing tape, the transfer cartridge having a reservoir, wherein the adhesive lancing tape and the transfer cartridge are positioned in the same horizontal plane relative to one another, and a frangible portion integrally formed between the transfer cartridge and the lancing tape such that the transfer cartridge and the lancing tape are detachably connected to one another via the frangible portion, the frangible portion including a sealing wall, the sealing wall configured such that upon breaking of the frangible portion to remove the transfer cartridge from the lancing tape, the sealing wall seals the reservoir, and wherein an inlet of the reservoir connected to the frangible portion is laterally offset from the target relative to a puncture direction of a puncturing element into the target, wherein the flow channel is configured to permit a blood sample to flow from the target and through the frangible portion before entering the transfer cartridge, wherein, in a first position when the transfer cartridge is connected to the lancing tape, the reservoir is configured to be in fluid communication with the flow channel, and wherein, in a second position when the transfer cartridge is disconnected from the lancing tape, the transfer cartridge is configured to be separated from the lancing tape; and a centrifuge having a receiving port adapted to receive the transfer cartridge, wherein with the transfer cartridge received within the centrifuge and a rotational force applied to the transfer cartridge, the centrifuge is configured such that the plasma portion of the blood sample is separated from the cellular portion through the reservoir.

15. The blood separation system of claim 14, wherein the lancing tape includes the adhesive on an inferior surface of the lancing tape.

* * * * *